(12) United States Patent
Piantoni et al.

(10) Patent No.: US 8,679,282 B2
(45) Date of Patent: Mar. 25, 2014

(54) MACHINE AND A METHOD FOR MANUFACTURING ABSORBENT ARTICLES

(75) Inventors: Matteo Piantoni, Albino (IT); Luca Pedretti, Crema (IT); Alberto Perego, Milan (IT)

(73) Assignee: GDM S.p.A. (IT)

( * ) Notice: Subject to any disclaimer, the term of this patent is extended or adjusted under 35 U.S.C. 154(b) by 1064 days.

(21) Appl. No.: 12/664,764

(22) PCT Filed: Jun. 16, 2008

(86) PCT No.: PCT/IB2008/001555
§ 371 (c)(1),
(2), (4) Date: Dec. 15, 2009

(87) PCT Pub. No.: WO2008/155618
PCT Pub. Date: Dec. 24, 2008

(65) Prior Publication Data
US 2010/0192739 A1 Aug. 5, 2010

(30) Foreign Application Priority Data
Jun. 19, 2007 (IT) .................... BO07A0431

(51) Int. Cl.
| B32B 37/00 | (2006.01) |
| B32B 37/02 | (2006.01) |
| B32B 38/00 | (2006.01) |
| B32B 38/04 | (2006.01) |
| B32B 38/10 | (2006.01) |
| B32B 38/18 | (2006.01) |

(52) U.S. Cl.
USPC ........... 156/265; 156/250; 156/256; 156/259; 156/269; 156/270; 156/510; 156/516; 156/517; 156/519; 156/521

(58) Field of Classification Search
USPC ......... 156/510, 516, 517, 519, 521, 250, 256, 156/259, 264, 265, 269, 270
See application file for complete search history.

(56) References Cited

U.S. PATENT DOCUMENTS 3,963,557 A 6/1976 Patterson
(Continued)

FOREIGN PATENT DOCUMENTS

| EP | 1719484 | 11/2006 |
| JP | 04-261655 | 9/1992 |

(Continued)

OTHER PUBLICATIONS

Written Opinion and Search Report of the European Searching Authority from counterpart PCT application, Dec. 29, 2008.
Observations by a Third Party from European Patent Office from counterpart application No. EP08762885, Jul. 12, 2013.
(Continued)

*Primary Examiner* — Mark A Osele
*Assistant Examiner* — Christopher C Caillouet
(74) *Attorney, Agent, or Firm* — Timothy J. Klima; Shuttleworth & Ingersoll, PLC

(57) ABSTRACT

Absorbent sanitary articles (2), such as nappies or incontinence pads with an elongated central body (2a) and at least one pair of closure tabs (5), are manufactured on a machine (1) by which the tabs (5) are directed in pairs from a feed unit (13) onto a transport line (6) carrying the articles (2) toward a sealing station. The feed unit (13) operates by making skew cross-cuts (16) in a continuous strip (15) of material, so as to generate a succession of tab elements (5) appearing trapezoidal in outline; the tab elements (5) are then distanced one from another in alternation along a direction (D3) transverse to their feed direction (D2) through the machine, so as to obtain two single columns (23) which are taken up by a roller (27) and aligned one with another so that the single tab elements (5) are ordered into a succession of transversely aligned pairs. The alignment roller (27) rotates tangentially to the transport line (6) and is timed to place one pair of tab elements (5) on each advancing article (2).

20 Claims, 7 Drawing Sheets

(56) References Cited

U.S. PATENT DOCUMENTS

| | | | |
|---|---|---|---|
| 5,224,405 A | 7/1993 | Pohjola | |
| 6,170,636 B1 | 1/2001 | Een | |
| 6,730,189 B1 | 5/2004 | Franzmann | |
| 7,918,961 B2 * | 4/2011 | Wada et al. | 156/259 |
| 2002/0175047 A1 | 11/2002 | Blumenthal | |
| 2008/0161766 A1 * | 7/2008 | Sablone et al. | 604/385.01 |
| 2008/0276439 A1 * | 11/2008 | Andrews et al. | 29/428 |

FOREIGN PATENT DOCUMENTS

| | | | |
|---|---|---|---|
| JP | 09-294769 | | 11/1997 |
| JP | 2003199790 | * | 7/2003 |
| JP | 2007-061462 | | 3/2007 |
| WO | 88/05416 | | 7/1988 |
| WO | 98/00356 | | 1/1998 |

\* cited by examiner

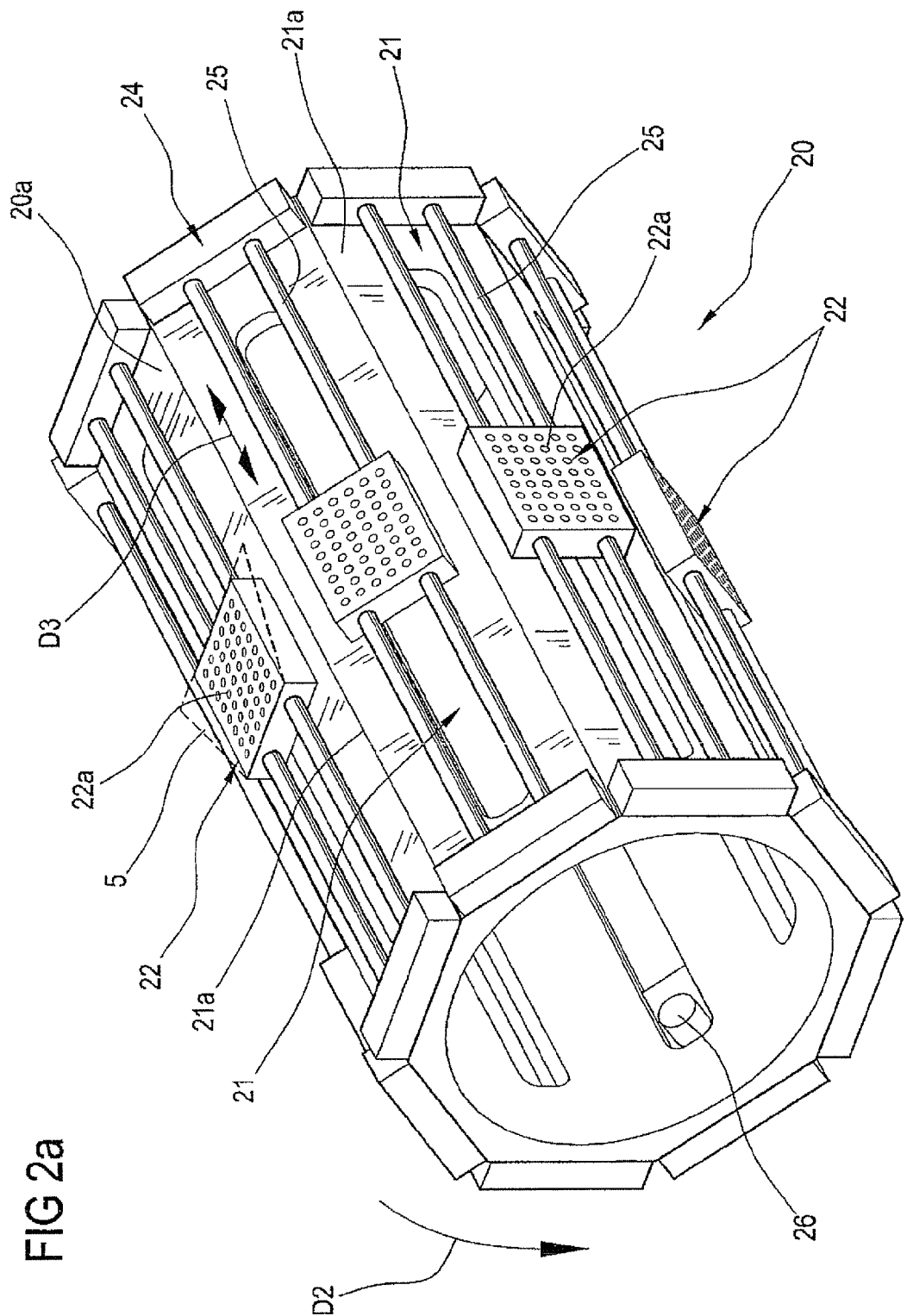

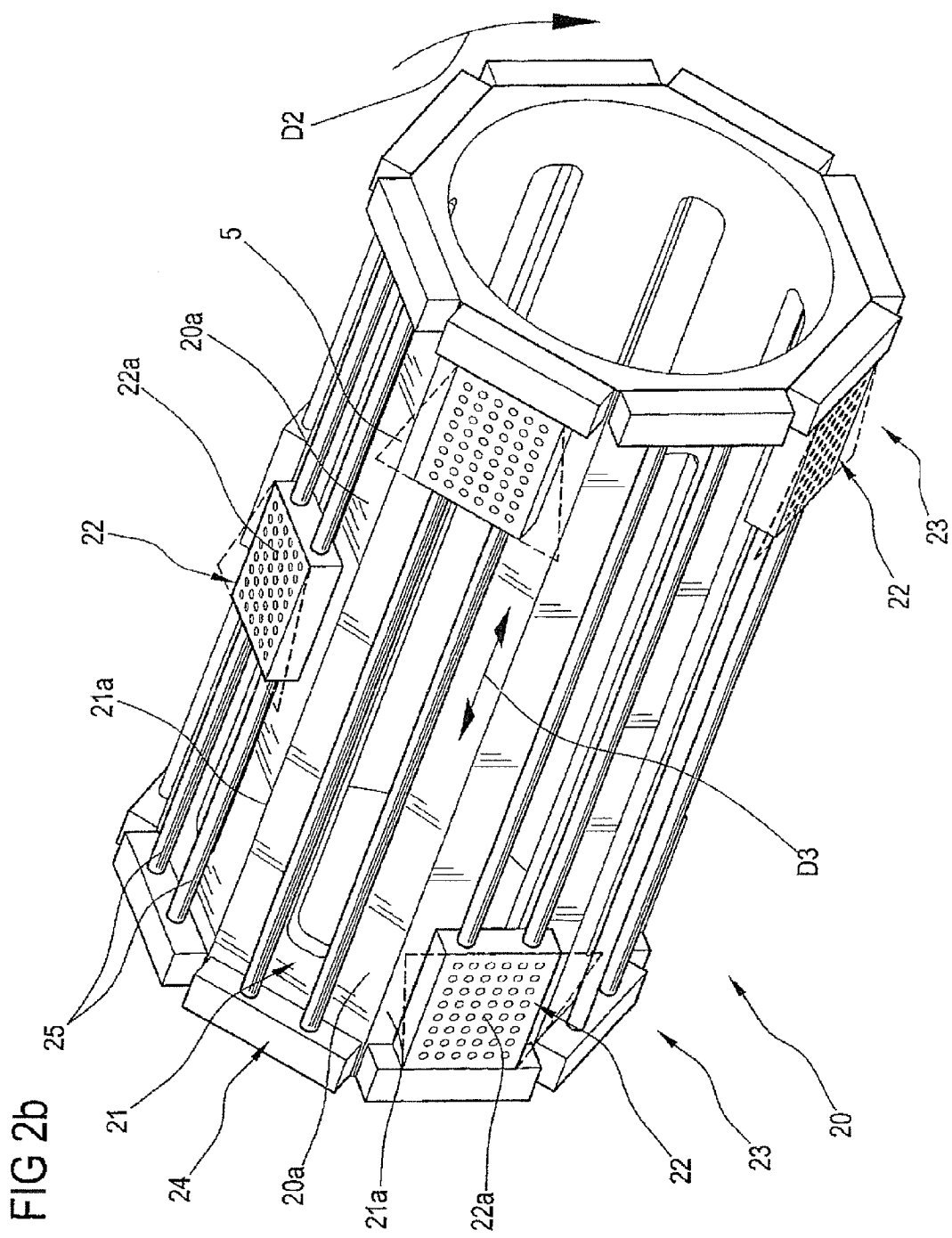

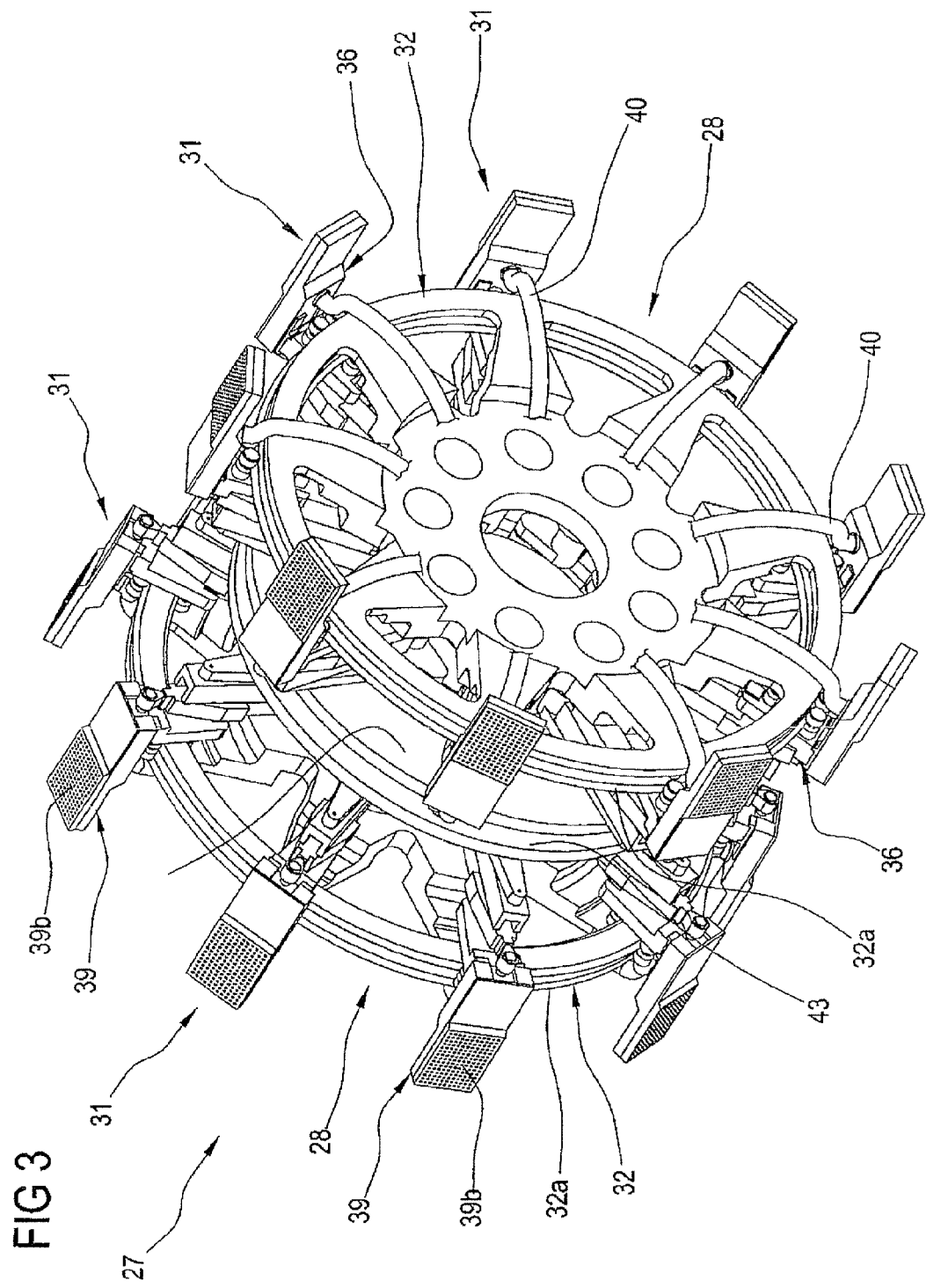

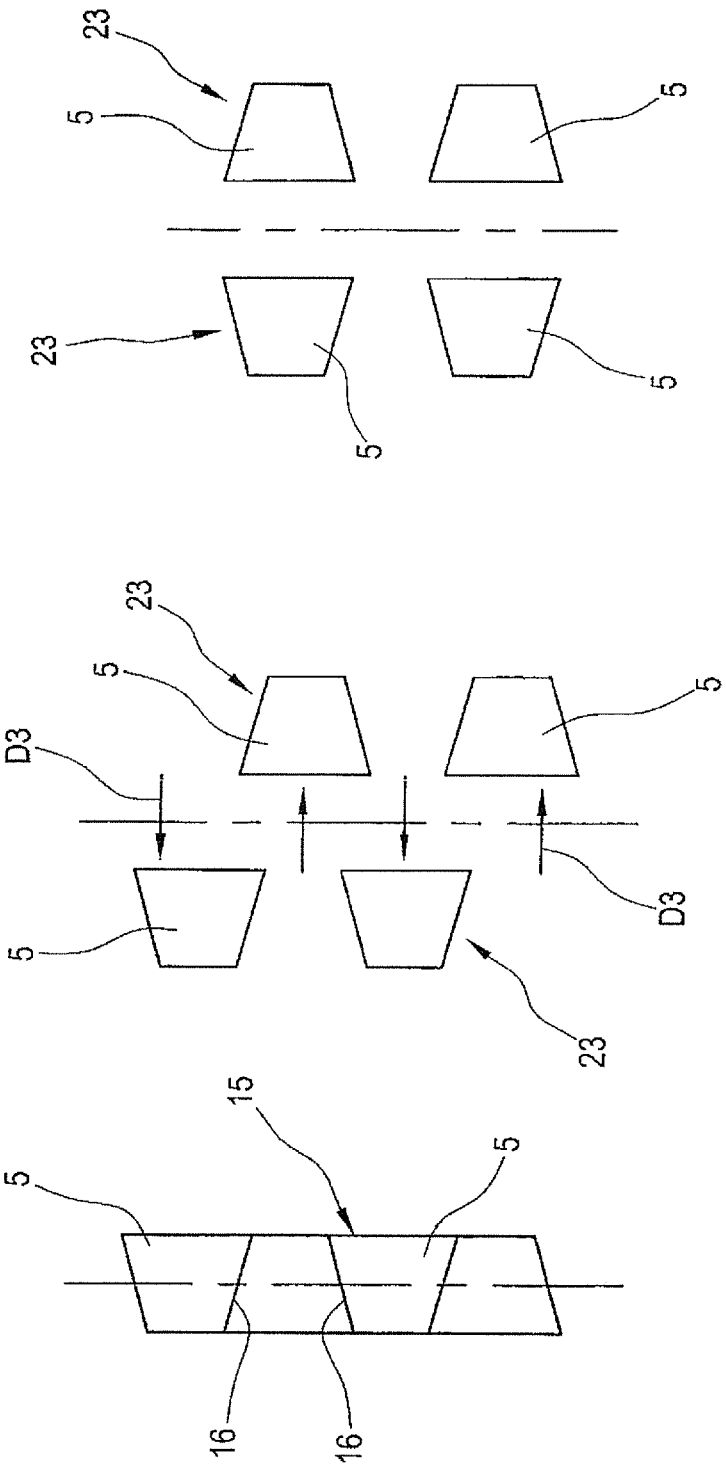

MACHINE AND A METHOD FOR MANUFACTURING ABSORBENT ARTICLES

This application is the National Phase of International Application PCT/IB2008/001555 filed Jun. 16, 2008 which designated the U.S. and that International Application was published under PCT Article 21(2) in English.

This application claims priority to Italian Patent Application No. BO2007A000431 filed Jun. 19, 2007, and PCT Application No. PCT/IB2008/001555 filed Jun. 16, 2008, which applications are incorporated by reference herein.

TECHNICAL FIELD

The present invention relates to a machine and to a method for manufacturing absorbent articles.

In particular, the invention is applicable preferably to the manufacture of disposable absorbent articles, typically nappies/diapers for babies, incontinence pads and similar sanitary items.

BACKGROUND ART

Conventionally, disposable sanitary products of the type in question comprise an absorbent pad, consisting normally of cellulose fibres, which is enclosed in a soft cover. The cover is fashioned from a permeable inner sheet of non-woven fabric and an impermeable outer sheet of polyethylene, bonded one to another and presenting shaped elasticated edges.

The absorbent article presents a front part and a rear part furnished with closure elements serving to ensure that the article will remain correctly and stably in place when put on by the wearer.

In particular, the closure elements consist in discrete strips or tabs of sheet elastomer material having at least one surface coated with adhesive and attachable thus to the front part of the absorbent article. The single article is furnished with a pair of such closure elements, positioned one on either side, by which the article is closed up and held in place, hugging the hips of the wearer.

Generally speaking, the closure elements are placed in pairs directly onto respective articles advancing continuously along a transport line.

More particularly, closure elements are obtained from a continuous strip of elastic material, fed through a first cutting station at which it is divided longitudinally to generate two continuous and parallel bands. The longitudinal cut follows a wavy line in such a way that one edge of each band will present a succession of projecting portions (each constituting a single closure element) alternated with recessed portions.

Thereafter, the two bands are advanced parallel one with another through a train of guide rollers, which also serve to align the two bands by accelerating or retarding the feed rate of at least one or the other. In this way, each projecting portion of one band will occupy a position facing a projecting portion of the other band.

Aligned thus, the bands advance toward a second cutting station at which they are divided into single segments, each presenting a respective projecting portion, in such a way as to obtain a succession of closure elements ordered in pairs. The pairs of elements are then directed onto the transport line along which the absorbent articles advance, and each successive pair is sealed to the rear part of a respective article.

In reality, machines of the prior art for manufacturing absorbent articles are affected by notable drawbacks.

Firstly, the machines in question are excessively cumbersome, due principally to the size of the components by which the single closure elements are formed. In effect, the closure elements are obtained from a pair of continuous bands that take up considerable amounts of space and require numerous rollers for conveying purposes.

Owing also to the nature of the elastic material from which the continuous strip is made, the bands tend not be accurately aligned.

In practice, the bands are tensioned by the guide rollers and this causes them to become staggered one relative to another, so that when cut transversely and fashioned into single closure elements, imprecisions will appear.

DISCLOSURE OF THE INVENTION

The object of the present invention is to provide a machine and a method for manufacturing absorbent articles, such as will be unaffected by the drawbacks mentioned above.

In particular, the object of the present invention is to provide a machine of compact dimensions for manufacturing absorbent articles.

A further object of the present invention is to provide a machine and a method for manufacturing absorbent articles that will be capable of aligning and subsequently feeding the single closure elements to a transport line with extreme precision.

The stated objects are realized in a machine and a method for manufacturing absorbent articles as characterized in any one or more of the appended claims.

BRIEF DESCRIPTION OF THE DRAWINGS

The invention will now be described in detail, by way of example, with the aid of the accompanying drawings, in which:

FIGS. 2*a* and 2*b* show a first constructional detail of the machine in FIG. 1, viewed in perspective and seen in two respective operating configurations;

FIG. 3 shows a second constructional detail of the machine in FIG. 1, viewed in perspective;

FIGS. 6*a*, 6*b* and 6*c* are schematic illustrations of operating steps in the process of forming tab closure elements destined for application to respective absorbent articles.

DETAILED DESCRIPTION OF THE PREFERRED EMBODIMENTS OF THE INVENTION

Figure 1:
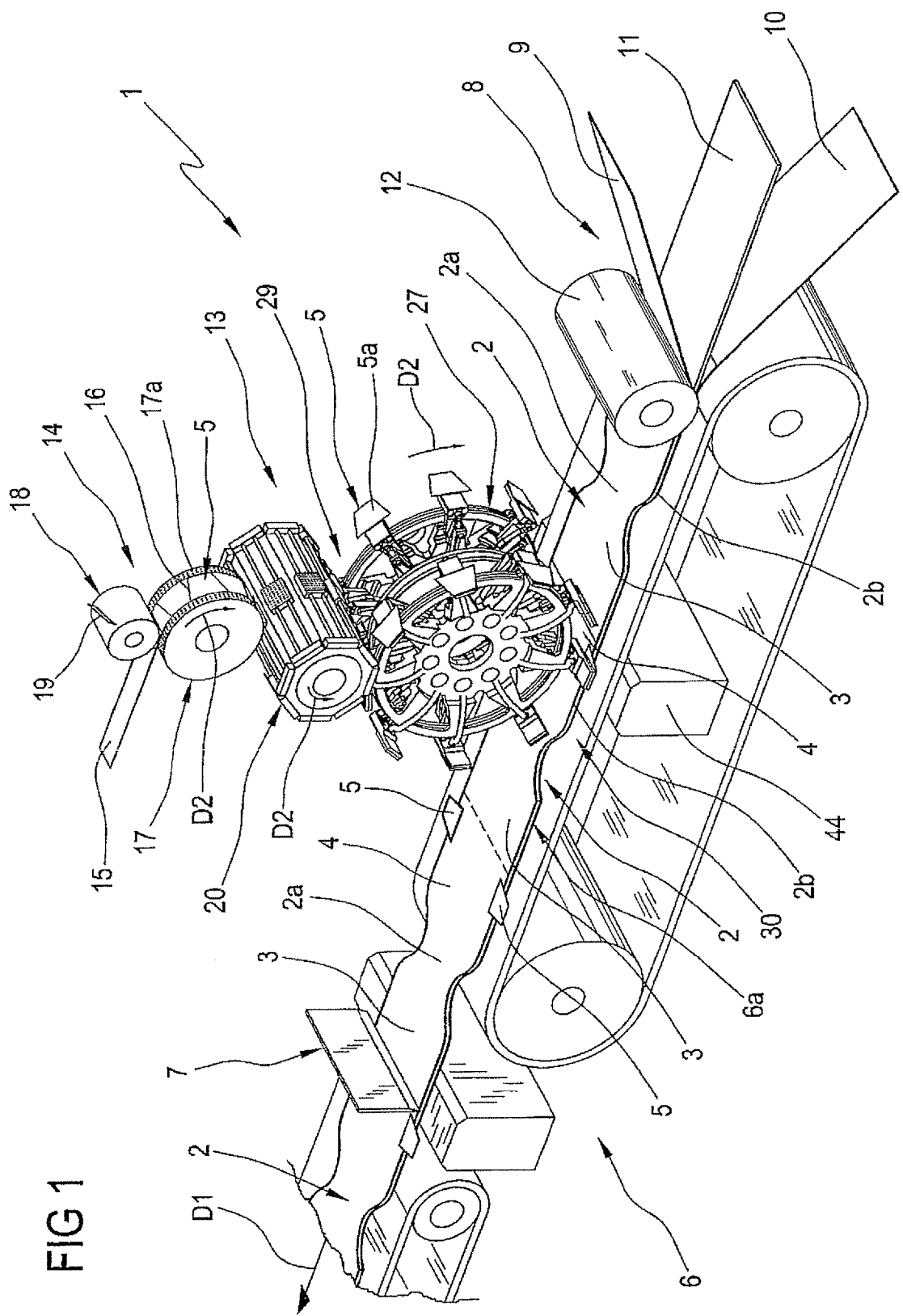
FIG. 1 shows a machine for manufacturing absorbent articles according to the present invention, viewed schematically and in perspective.

With reference to FIG. 1, numeral 1 denotes a machine, in its entirety, for manufacturing absorbent articles 2. In particular, albeit with no limitation in scope intended, the machine 1 illustrated in FIG. 1 is designed to manufacture absorbent articles 2 such as nappies/diapers for babies or incontinence pads for adults.

The absorbent article 2, illustrated schematically in FIG. 1, comprises an elongated central body 2*a* extending predominantly along a respective longitudinal axis. The central body 2*a* is of substantially rectangular outline, with the two longitudinal sides 2*b* presenting respective inwardly directed curved contours to accommodate the legs of the wearer.

The absorbent article 2 also presents a front portion 3, destined to make contact with the abdominal region of the wearer when the article 2 is in use, and a rear portion 4, opposite to the front portion, destined to make contact with the lumbar region of the wearer.

As illustrated to advantage in FIG. 1, the article 2 is also furnished with two tab closure elements 5 extending laterally from the rear portion 4 and designed, in use, to overlap respective lateral areas of the front portion 3, thereby securing the absorbent article 2 around the body of the wearer. The tab elements 5 consist in discrete cuts of sheet material, preferably an elastic material such as will favour a close fit around the hips of the wearer.

Alternatively, articles 2 may be furnished with two pairs of tab closure elements 5, one associated with the front portion 3 and another with the rear portion 4. In this instance, the pair of elements 5 associated with the front portion 3 can be attached removably to the pair of elements 5 associated with the rear portion 4.

Preferably, each element 5 presents a contact surface 5a rendered stickable by the application of an adhesive substance to the selfsame surface. Alternatively, each of the closure elements 5 might be fastenable to the front portion 3 by means of a tab faced with Velcro®. In this instance, the contact surface 5a of each tab element 5 and the front portion 3 of the article will be furnished respectively with a fabric presenting a plurality of loops and a fabric presenting a plurality of hooks, or vice versa.

Still referring to FIG. 1, the machine 1 comprises a transport line 6 along which the articles 2 advance in a predetermined direction denoted D1. The transport line 6 is designed preferably to feed a continuous strip 6a of material toward a relative cutting station 7, where the strip 6a is divided into discrete lengths each providing a single absorbent article 2.

The continuous strip 6a is prepared at an assembly station denoted 8, where a first strip 9 of impermeable material is joined to a second strip 10 of permeable material. Sandwiched between the two strips 9 and 10 is an absorbent material 11 such as will retain body fluids released by the wearer. As indicated schematically in FIG. 1, the longitudinal edges of the strips 9 and 10 making up the continuous strip 6a of absorbent articles 2 are bonded together and shaped by a forming roller denoted 12.

Operating between the assembly station 8 and the cutting station 7 is a feed unit 13 by which pairs of tab closure elements 5 are first prepared and then positioned on the strip 6a of absorbent articles 2.

In detail, the feed unit 13 comprises a cutter device 14 positioned to receive a continuous strip 15 of elastic sheet material in which it produces a succession of transverse cuts 16 designed to generate a corresponding succession of tab closure elements 5.

The cutter device 14 comprises a first roller 17 and a second roller 18 contrarotating tangentially one to another so as to advance the succession of elements 5 along a respective feed direction D2.

In particular, the first roller 17 presents a cylindrical aspirating surface 17a on which the aforementioned succession of tab closure elements 5 is retained and transported. The second roller 18 presents at least one pair of blades 19 deployable against the strip 15 retained on the aforementioned aspirating surface 17a of the first roller 17 in such a way as to produce the transverse cuts 16.

The blades 19 are set skew one to another and angled transversely in relation to a rotational axis of the second roller 18. Accordingly, the cuts 16 are made obliquely to the longitudinal dimension of the continuous strip 15, so that each successive pair of cuts 16 will appear mutually convergent, and not parallel.

The strip 15 is therefore cross-cut repeatedly to produce a succession of tab elements 5 appearing substantially trapezoidal in outline.

Reference is made in the present specification to elements 5 of trapezoidal geometry purely by way of example, with no limitation in scope of the invention implied. Nonetheless, the tab elements 5 could in practice be of any given shape, depending on the particular manufacturing requirements.

Operating downstream of the first roller 17 is a separation roller 20 placed to receive the succession of tab elements 5 and designed to distance each element 5 from the element 5 next in sequence during the course of their progress along the aforementioned feed direction D2.

In particular, the separation roller 20 presents a substantially cylindrical outer surface 20a revolving tangentially to the aspirating surface 17a of the first roller 17 and affording a plurality of slots 21 occupiable by respective tab closure elements 5.

As shown to better advantage in FIGS. 2a and 2b, each slot 21 serves to accommodate one respective element 5 and is distanced from the adjacent slot 21 by an angled portion 21a of the substantially cylindrical surface 20a.

In more detail, each of the slots 21 is equipped with a slide 22 traversable along a respective direction D3 parallel to a rotational axis of the separation roller 20. Advantageously, during the rotation of the separation roller 20, the slides 22 are capable of movement between a first position of substantial alignment one with another (FIG. 2a), in which the tab elements 5 are received in succession from the first roller 17, and a second position in which each slide 22 is staggered relative to the next slide in sequence (FIG. 2b).

Importantly, each slide 22 traverses in a direction opposite to the next slide 22 in sequence, the two always moving away from or toward one other. Accordingly, when the slides 22 occupy the aforementioned second position, they will generate two columns 23 of tab elements 5 advancing in staggered formation.

Moreover, the slides 22 are operated in such way as to arrange the elements 5 of each relative column 23 with their respective longer sides directed toward the elements 5 of the other column 23.

Each slide 22 presents an aspirating surface 22a proportioned to retain the respective tab element 5 at least in part. Still referring to FIGS. 2a and 2b, the aspirating surface 22a presents a substantially rectangular outline delimiting an area on which only a central portion of the respective tab closure element 5 is retained. In this situation, each trapezoidally shaped element 5 advances with the two obliquely cut opposite sides projecting laterally from the slide 22 and lying above the aforementioned angled portions 21a.

It will be seen also that the aspirating surfaces 22a of the slides 22 occupy respective planes disposed transversely one to another and tangential to the outer surface 20a of the separation roller 20. Consequently, the single tab elements 5 taken up from the first roller 17 onto the separation roller 20 likewise occupy respective planes disposed transversely one to another. Thus, when the slides 22 are traversed along the aforementioned direction D3 away from one another, the lateral portions of consecutive elements 5 will not interfere one with another.

In an alternative embodiment, each slide 22 could be traversed in the direction opposite to that indicated in FIG. 6b. In this instance, the tab elements 5 would be applied to the strip 6a in a position turned through 180° relative to that of FIG. 1, that is to say with the shorter sides of the elements 5 directed toward the middle of the strip 6a, rather than away from the strip.

Each slide 22 further comprises actuator means 24 by which it is traversed between the first position and second position as the separation roller 20 rotates on its axis.

In particular, the actuator means 24 comprise a plurality of slide ways 25, arranged in pairs, each associated with a respective slot 21. Each slide way 25 presents a substantially cylindrical appearance and extends along the aforementioned direction D3, parallel to the rotational axis of the separation roller 20.

Each slide 22 is coupled operatively to the respective pair of ways 25 and traversable thus along the ways in the aforementioned direction D3.

The actuator means 24 comprise a plurality of cam follower rollers 26, each associated with the underside of a respective slide 22 and inducing motion in the selfsame slide along the ways 25.

To advantage, each roller 26 engages the profile presented by a fixed cam of conventional embodiment (not illustrated), which establishes a predetermined trajectory to be described by each slide 22 when the separation roller 20 is set in rotation.

Thus, the slides 22 are brought into alignment one with the next by the respective cam follower rollers 26 when passing tangentially to the first roller 17 (FIG. 2a), each positioned to take up a respective tab closure element 5. As the slides 22 approach an alignment roller denoted 27, sideways motion is induced in each one by the relative cam follower roller 26 (FIG. 2b), in such a way as to form the aforementioned columns 23 of elements 5 on the alignment roller 27.

In particular, the roller 27 in question operates downstream of the separation roller 20 and serves to align the two columns 23 of tab closure elements 5 so that the elements 5 advance ordered in successive pairs.

As illustrated in FIG. 1, the alignment roller 27 rotates tangentially to the transport line 6 on which the strip 6a advances, and will place one pair of tab elements 5 on each respective article 2.

More exactly, and as illustrated to advantage in FIG. 3, the alignment roller 27 comprises a pair of drums 28 disposed parallel one with another and rotating tangentially to the separation roller 20. The drums 28 rotate between a transfer station 29 at which the tab elements 5 are taken up, and a release station 30 at which the pairs of elements 5 are placed on the absorbent articles 2.

The drums 28 are coupled together and present a set of retaining and motion inducing mechanisms 31, each designed to take up the single tab elements 5 of a respective column 23.

Each drum 28 further presents a wheel 32 carrying the respective retaining mechanisms 31 and aligned concentrically on a rotational axis of the alignment roller 27 as a whole.

Figure 4:
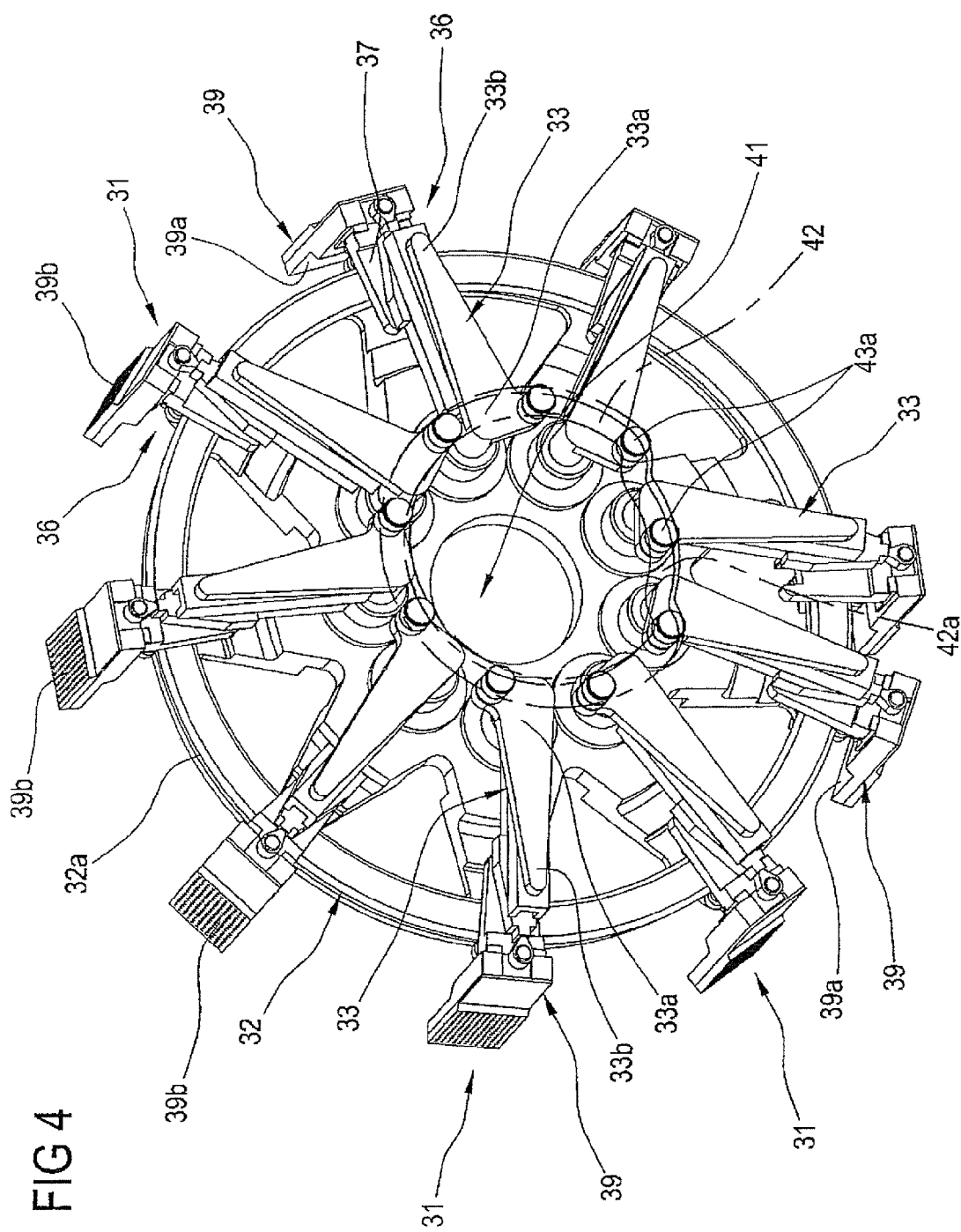
FIGS. 4 and 5 are respective enlarged fragments of the constructional detail illustrated in FIG. 3, shown with certain parts omitted better to reveal others.
Figure 5:
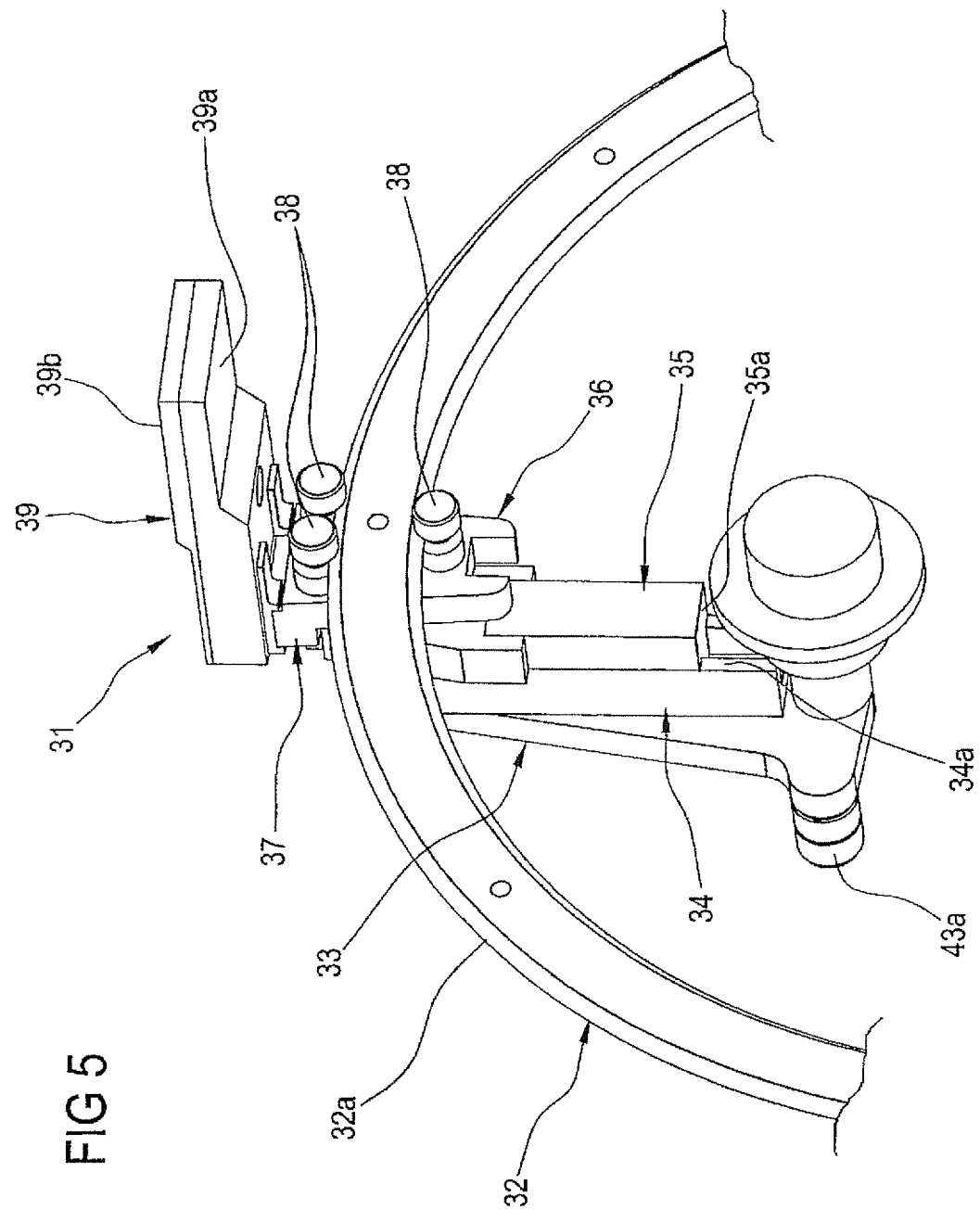

As illustrated to advantage in FIGS. 4 and 5, each retaining and motion-inducing mechanism 31 consists in a rod 33 of which a first end 33a is associated pivotably with the respective wheel 32, and a second end 33b opposite to the first end 33a occupies a position coinciding with the periphery of the wheel 32.

The rod 33 presents two portions 34 and 35, coupled telescopically in such a way that the length of the rod 33 can be varied, as will be described in due course. A first portion 34 of the rod 33 incorporates the first end 33a, whilst a second portion 35 incorporates the second end 33b. As illustrated to advantage in FIG. 5, the first portion 34 presents a longitudinal cavity 34a slidably accommodating an elongated element 35a that forms a part of the second portion 35. With the second portion 35 thus capable of sliding in relation to the first portion 34, advantageously, the rod 33 can be extended in a direction coinciding with its longitudinal dimension.

Referring in particular to FIG. 4, which shows just one of the drums 28 with certain parts cut away better to illustrate the carrier wheel 32 and the respective retaining mechanisms 31, it will be seen that the first ends 33a of the rods 33 are arranged around a circumferential path aligned concentrically on a rotational axis of the wheel 32.

The wheel 32 also presents a peripheral rim 32a of circular geometry and, associated slidably with the rim, a plurality of trolleys 36 each coupled to the second end 33b of a respective rod 33.

In particular, each trolley 36 (FIG. 5) presents a bracket 37 rigidly associated with the second portion 35, also three roller wheels 38 mounted rotatably to the bracket 37 and running on the rim 32a of the wheel 32.

Each mechanism 31 further comprises a bearer element 39 likewise rigidly associated with the bracket 37, located above the trolley 36 and presenting a substantially parallelepiped, flat appearance.

The bearer element 39, which lies outside the circumference of the relative wheel 32, presents a bottom face 39a associated with the bracket 37, and an aspirating face 39b on the side opposite to the bottom face 39a.

The aspirating face 39b presents a substantially rectangular outline referable to a predominating axis that extends parallel to the rotational axis of the alignment roller 27.

The bearer element 39 is also associated with a vacuum duct 40 by which the aforementioned aspirating face 39b is placed in fluid communication with a source of negative pressure (not illustrated). As illustrated in FIG. 3, each duct 40 is positioned externally of the relative drum 28, extending in a radial direction relative to the selfsame drum 28.

Thus, when each retaining mechanism 31 draws into alignment with the transfer station 29, a single tab closure element 5 will be taken up and held on the aspirating face 39b of the respective bearer element 39.

The alignment roller 27 further comprises means 41 by which motion is induced in the retaining mechanisms 31, causing the selfsame mechanisms 31 to rotate about the first ends 33a of the respective rods 33. The rotation in question is effected simultaneously with the rotation of the wheels 32 between the transfer station 29 and the release station 30.

More exactly, the motion-inducing means 41 in question present a pair of cam profiles 42, of which one only is indicated schematically in FIG. 4, purely by way of example.

Each cam profile 42 is incorporated into a fixed cylindrical mounting 43 interposed between the two drums 28 and coaxial with the carrier wheels 32. In this way, each cam profile 42 is positioned facing a respective wheel 32 on the side of the selfsame wheel 32 remote from the aforementioned ducts 40.

The motion-inducing means 41 further comprise a plurality of cam follower rollers 43a, each one of which associated freely with a respective rod 33 and in engagement operatively with a corresponding cam profile 42. In this situation, when the aforementioned carrier wheels 32 are set in rotation, the cam follower rollers 43a of the relative retaining mechanisms 31 will roll internally of the corresponding cam profile 42.

To advantage, the cam profile 42 describes a substantially circular trajectory presenting an inwardly oriented arcuate portion 42a that serves to induce a predetermined movement of the retaining mechanisms 31. More exactly, when a cam follower roller 43a passes along the arcuate portion 42a, the corresponding mechanism 31 is made to pivot about the first end 33a of the arm, causing the trolley 36 to roll along the peripheral rim 32a of the relative wheel 32. As a result, the rod extends 33, and the aforementioned portions 34 and 35 are distanced one from another.

Consequently, the retaining mechanisms 31 are made to shift further between a first position in which the respective bearer element 39 is staggered relative to the bearer element 39 of the adjacent drum 28 in order to take up the elements 5 of the two columns 23 at the transfer station 29, and a second position in which the bearer elements 39 of the two drums 28 are aligned at the release station 30 so that successive pairs of tab elements 5 can be placed on the rear portions 4 of respective absorbent articles 2.

The machine 1 further comprises a sealing unit 44 stationed on the transport line 6, by which the single tab elements 5 of each pair are bonded to the corresponding absorbent article 2. The sealing unit 44 is not described in detail, being of familiar type, but will consist preferably of an ultrasonic welding device able to secure the tab closure elements 5 stably to the continuous strip 6a.

The sequence of steps involved in fashioning the single tab elements 5 will now be described, with reference to the examples of FIGS. 6a, 6b and 6c.

In a first step, transverse cuts 16 are made in the continuous strip 15 to generate a succession of tab closure elements 5 (FIG. 6a). The step in question involves making a succession of skew cross-cuts 16 in the strip 15, generating tab elements 5 of trapezoidal outline.

Next, the elements 5 are distanced one from another so as to form two columns 23 of elements 5 (FIG. 6b).

This step, performed by the separation roller 20 described previously, is accomplished by traversing each tab element 5 along a direction D3 transverse to the feed direction D2 of the selfsame elements 5. The separation step has the effect of staggering the single elements 5 of each column 23 relative to the elements 5 of the other column 23.

Thereafter, the two columns 23 are mutually aligned so as to order the tab elements 5 into a succession of pairs, that is to say, with each element 5 of one column 23 lying directly alongside an element 5 of the other column 23 (FIG. 6c).

In particular, the retaining mechanisms 31 of one respective drum 28 are caused to pivot on the first ends 33a of the rods 33 and thus displaced along the feed direction D2 of the tab elements 5, which undergo a slight acceleration as a result; at the same time, the retaining mechanisms 31 of the other drum 28 are displaced in the opposite direction to the aforementioned feed direction D2, thereby decelerating the respective tab elements 5.

Thus, the mechanisms 31 advancing between the transfer station 29 and the release station 30 are aligned in such a manner as to order the tab closure elements 5 into a succession of pairs, as aforementioned.

Advantageously, depending on the shape of the two cam profiles 42 presented by the cylindrical mounting 43, the aligned pairs of elements 5 can be distanced one from the next by a predetermined interval at the release station 30.

In other words, the pitch at which successive pairs of tab elements 5 are released to the absorbent articles 2 can be geared to the length of the single article 2, simply by selecting a suitable geometry for the cam profile 42.

To advantage, the machine 1 disclosed is of notably compact dimensions. In effect, the single tab closure elements 5 are prepared and supplied by a feed unit 13 consisting simply of mutually tangential rollers. The advantage in question is gained by virtue of the fact that the strip 15 is cut into single elements immediately on entering the unit 13. This means that the continuous strip material used to prepare the tab closure elements 5 can be fed and processed without the need for unduly large operating spaces.

Moreover, the elements 5 are aligned with extreme accuracy, as the continuous strip 15 is not routed through trains of guide rollers. In practice, the alignment step is effected immediately after the cutting step, simply by causing the columns 23 of single elements 5 to advance at different speeds.

The invention claimed is:

1. A machine for manufacturing absorbent articles which include an elongated central body and at least one pair of tab closure elements, the machine including a transport line along which the absorbent articles advance in a predetermined feed direction, and a feed unit by which pairs of the tab closure elements are associated with each of the absorbent articles, wherein the feed unit comprises:
   a cutter device by which successive transverse cuts are made in a continuous strip of material to produce a succession of single tab closure elements;
   a separation roller, operating downstream of the cutter device and placed to receive the succession of single tab closure elements, by which each element is distanced from a next element in sequence, the separation roller comprising a plurality of slides traversable along respective directions parallel to a rotational axis of the separation roller, wherein, during rotation of the separation roller, the slides are movable between:
      a receiving position, in which each slide receives a respective single tab closure element and is aligned at least with an adjacent slide which is about to receive a subsequent single tab closure element, and
      a releasing position, located downstream of the receiving position and in which each slide is staggered relative to the next slide in sequence and approaches the alignment roller to release the respective single tab closure elements onto the alignment roller, wherein the slides occupying the releasing position define two spaced apart columns of tab closure elements advancing in a staggered formation; and
   an alignment roller, operating downstream of the separation roller and rotating tangentially to the transport line, the alignment roller being configured to take up the staggered tab closure elements released from the slides of the separation roller, order the taken up staggered tab closure elements into a succession of pairs advancing two abreast, and then place each successive pair of tab closure elements on a respective absorbent article advancing along the transport line.

2. The machine of claim 1, wherein the cutter device comprises:
   a first roller presenting an aspirating surface on which the continuous strip is retained,
   a second roller contrarotating tangentially to the first roller and presenting at least one pair of blades deployable against the strip retained on the aspirating surface in such a way as to divide it into a succession of tab closure elements.

3. The machine of claim 2, wherein each blade extends transversely to a rotational axis of the second roller and produces a cut generated obliquely to the longitudinal dimension of the strip, in such a way that each tab closure element presents a substantially trapezoidal outline.

4. The machine of claim 2, wherein the separation roller presents a substantially cylindrical outer surface revolving tangentially to the aspirating surface of the first roller and including a plurality of slots distanced one from a next, arranged in succession around an entire circumference of the roller, each of which is occupied by a respective tab closure element.

5. The machine of claim 4, wherein each slot comprises one of the slides.

6. The machine of claim 5, wherein each slide includes an aspirating surface for retaining a respective tab closure element at least in part, and is associated with an actuator mechanism for traversing the slide between the receiving position and the releasing position.

7. The machine of claim 6, wherein the aspirating surface receives a central portion of a respective tab closure element, such that each tab closure element presents two obliquely cut opposite sides projecting laterally from the slide.

8. The machine of claim 7, wherein the alignment roller comprises a pair of drums disposed parallel one with another, revolving tangentially to the separation roller and rotatable between a transfer station at which the tab closure elements are taken up, and a release station at which the tab closure elements are placed on the absorbent articles.

9. The machine of claim 8, wherein each drum comprises a plurality of retaining mechanisms for retaining and inducing motion in the tab closure elements of a respective column and a wheel on which the retaining mechanisms are carried.

10. The machine of claim 9, wherein each retaining mechanism comprises:
a rod including a first end associated pivotably with the wheel and a second end attached to a trolley running on a peripheral rim of the wheel;
a bearer element including a bottom face associated with the trolley and an aspirating face on a side opposite the bottom face for retaining the tab closure elements.

11. The machine of claim 10, wherein the first end of each rod coincides positionally with a circumferential path aligned concentrically on the rotational axis of the respective wheel, and the rod includes two portions coupled telescopically one to another such that a length of the rod is variable.

12. The machine of claim 10, wherein the alignment roller further comprises a motion inducing mechanism by which motion is induced in the retaining mechanisms to rotate the retaining mechanisms about the first ends of the respective rods during the rotation of each wheel between the transfer station and the release station.

13. The machine of claim 12, wherein the motion inducing mechanism comprises a pair of cam profiles, each facing a respective wheel, and each retaining mechanism of one respective drum is associated operatively with a relative cam profile to rotate between a first position staggered relative to a bearer element of the other drum, in which respective tab closure elements are taken up at the transfer station and a second position of alignment with the bearer element of the other drum, in which the tab closure elements are freed in succession at the release station and placed on the absorbent articles.

14. The machine of claim 13, and further comprising a sealing unit positioned on the transport line, by which the tab closure elements of each pair are secured to a corresponding absorbent article.

15. A method for manufacturing absorbent articles which include an elongated central body and at least one pair of tab closure elements, comprising:
providing a machine including:
a transport line along which the absorbent articles advance in a predetermined feed direction, and a feed unit by which pairs of the tab closure elements are associated with each of the absorbent articles,
wherein the feed unit comprises:
a cutter device by which successive transverse cuts are made in a continuous strip of material to produce a succession of single tab closure elements:
a separation roller, operating downstream of the cutter device and placed to receive the succession of single tab closure elements, by which each element is distanced from a next element in sequence, the separation roller comprising a plurality of slides traversable along respective directions parallel to a rotational axis of the separation roller, wherein, during rotation of the separation roller, the slides are movable between:
a receiving position, in which each slide receives a respective single tab closure element and is aligned at least with an adjacent slide which is about to receive a subsequent single tab closure element, and
a releasing position, located downstream of the receiving position and in which each slide is staggered relative to the next slide in sequence and approaches the alignment roller to release the respective single tab closure elements onto the alignment roller, wherein the slides occupying the releasing position define two spaced apart columns of tab closure elements advancing in a staggered formation; and
an alignment roller, operating downstream of the separation roller and rotating tangentially to the transport line, the alignment roller being configured to take up the staggered tab closure elements released from the slides of the separation roller, order the taken up staggered tab closure elements into a succession of pairs advancing two abreast, and then place each successive pair of tab closure elements on a respective absorbent article advancing along the transport line;
advancing the absorbent articles in succession along the predetermined feed direction, associating the pairs of tab closure elements with each of the absorbent articles, and sealing each pair of tab closure elements to a respective one of the absorbent articles;
wherein the associating the pairs of tab closure elements with the absorbent articles includes:
making the successive transverse cuts in the continuous strip of material to create the succession of single tab closure elements;
distancing the tab closure elements one from another to form the two spaced apart columns of the tab closure elements;
aligning the two spaced apart columns of the tab closure elements to order the tab closure elements in the succession of pairs.

16. The method of claim 15, wherein the making the series of transverse cuts involves cross-cutting the continuous strip repeatedly in such a way as to generate the succession of single tab closure elements each presenting a substantially trapezoidal outline.

17. The method of claim 15, wherein the distancing the tab closure elements one from another involves displacing each element along a direction transverse to a feed direction along which the tab closure elements are caused to advance.

18. The method of claim 15, wherein the aligning the two spaced apart columns includes at least one chosen from accelerating and decelerating the advance of at least one of the two spaced apart columns to position each tab closure element of one of the two spaced apart columns alongside a corresponding tab closure element of the other of the two spaced apart columns.

19. The method of claim 15, wherein the aligning the two spaced apart columns includes accelerating the advance of one of the two spaced apart columns and decelerating the advance of the other of the two spaced apart columns to position each tab closure element of the one of the two spaced apart columns alongside a corresponding tab closure element of the other of the two spaced apart columns.

20. The method in claim 15, wherein the associating the pairs of tab closure elements with the absorbent articles includes distancing each pair of tab closure elements from a next pair of tab closure elements in sequence and placing the each pair of tab closure elements on the respective absorbent article.

\* \* \* \* \*